United States Patent [19]

Nishizawa et al.

[11] Patent Number: 5,405,763

[45] Date of Patent: Apr. 11, 1995

[54] GENE ENCODING ASYMMETRICALLY ACTIVE ESTERASE

[75] Inventors: Masako Nishizawa, Takarazuka; Hideo Okawa, Ashiya; Masaharu Kanaoka, Toyonaka, all of Japan

[73] Assignee: Sumitomo Chemical Company, Limited, Osaka, Japan

[21] Appl. No.: 817,917

[22] Filed: Jan. 9, 1992

[30] Foreign Application Priority Data

Jan. 10, 1991 [JP] Japan .................................. 3-001537

[51] Int. Cl.$^6$ ...................... C12N 15/55; C12N 15/70; C12N 9/18; C12P 7/40
[52] U.S. Cl. .................................. 435/136; 435/197; 435/69.1; 435/172.3; 435/252.3; 435/252.33; 435/320.1; 536/23.2; 935/14; 935/29; 935/56; 935/72; 935/73
[58] Field of Search .................. 435/136, 197, 69.1, 435/252.3, 252.33, 320.1, 172.3; 536/23.2; 935/14, 29, 56, 72.23

[56] References Cited

FOREIGN PATENT DOCUMENTS 0264457 4/1988 European Pat. Off. .
0299558 1/1989 European Pat. Off. .
59-210892 11/1984 Japan .
1-181788 7/1989 Japan .

OTHER PUBLICATIONS

J. Sambrook et al. "Molecular Cloning: A Laboratory Manual" Cold Spring Harbor Lab. Press pp. 17.1–17.44 (Oct. 1989).
Mitsuda, S. et al. "Microbial Stereoselective Hydrolysis of . . . " Chemical Abstracts 116:12688s (Apr. 1991).
ATCC 1989 Catalog p. 97 entry #53323 Pharmacia 1984 Catalog p. 63.
Deutscher M. (ed). "Guide to Protein Purification" Meth. in Enzymol. vol. 182 pp. 602–613, 738–751 (1990).
Belyavsky, A. et al. "PCR-based cDNA library construction: . . . " Nuc. Acids Res. 17(8) 2919–2932 (Apr. 1989).
Berger, S. L. et al. (eds.) "Guide to Molecular Cloning Techniques". Meth. in Enzymol. vol. 152 pp. 393–399, 415–423, 432–447, 661–704 (1987).
Chemical Abstract, vol. 112, No. 13, 26 Mar. 1990, Sugimoto, M. et al., pp. 610 & JP-A-1 181 788, Jul. 1989.
Chemical Abstract, vol. 118, No. 3, 18 Jan. 1993, Mitsuta, Masaru et al., pp. 583 & JP-A-4 234 991, Aug. 1992.

Primary Examiner—Robert A. Wax
Assistant Examiner—Rebecca Prouty
Attorney, Agent, or Firm—Birch, Stewart, Kolasch & Birch

[57] ABSTRACT

An isolated gene encoding an esterase capable of asymmetrically hydrolysing an ester of chrysanthemic acid or its derivative to give an intermediate useful for the production of pharmaceutically and/or agriculturally useful compounds, expression plasmids containing said gene, microorganisms transformed with said expression plasmids, and the production of the esterase by culturing said transformants.

19 Claims, 6 Drawing Sheets

```
GGTACCGCTA CCTTTTCATG CACCCCAGCG GTGAGGACCT GAAATTCCTG TCACGCCTGG      60
TTTCCGAGGG GAAACTGCAA CCCGTGGTGG ACAGCAGCTA TCCGCTCGAA AAGATCGGCG     120
ACGTTTCGCC GCGCTGGAGC AGGGACGCGC CAAGGGCAAG ATCGTGGTGA CCATGGACAC    180
GCGCGGCAGT TAGGCAGTTA GGCTGTCCGG GTG GAT GCA CAG ACG ATT GCC CCT    234
                                  Met Asp Ala Gln Thr Ile Ala Pro
                                                      5

GGA TTC GAA TCA GTC GCC GAA CTC TTT GGC CGT TTC CTG AGC GAA GAC      282
Gly Phe Glu Ser Val Ala Glu Leu Phe Gly Arg Phe Leu Ser Glu Asp
         10                  15                  20

CGG GAA TAT TCA GCC CAG CTC GCG GCC TAC CAC CGC GGA GTC AAG GTA      330
Arg Glu Tyr Ser Ala Gln Leu Ala Ala Tyr His Arg Gly Val Lys Val
 25                  30                  35                  40

TTG GAC ATC AGC GGT GGG CCG CAC CGC CGC CCG GAT TCC GTG ACC GGT      378
Leu Asp Ile Ser Gly Gly Pro His Arg Arg Pro Asp Ser Val Thr Gly
                 45                  50                  55

GTT TTC TCC TGC TCC AAG GGA GTA TCC GGG CTG GTC ATC GCA CTT TTG      426
Val Phe Ser Cys Ser Lys Gly Val Ser Gly Leu Val Ile Ala Leu Leu
             60                  65                  70

GTC CAG GAC GGC TTC CTC GAC CTC GAC GCC GAA GTG GTC AAG TAC TGG      474
Val Gln Asp Gly Phe Leu Asp Leu Asp Ala Glu Val Val Lys Tyr Trp
         75                  80                  85

CCG GAA TTC GGC GCC GAA GGA AAG GCC ACG ATT ACC GTG GCC CAG CTG      522
Pro Glu Phe Gly Ala Glu Gly Lys Ala Thr Ile Thr Val Ala Gln Leu
     90                  95                 100

CTC TCC CAC CAG GCC GGG CTT CTG GGA GTC GAA GGC GGA CTC ACC CTC      570
Leu Ser His Gln Ala Gly Leu Leu Gly Val Glu Gly Gly Leu Thr Leu
105                 110                 115                 120
```

FIG.1(a)

```
GCG GAA TAC AAC AAC TCC GAA CTG GCC GCC GCC AAG CTC GCG CAG ATG        618
Ala Glu Tyr Asn Asn Ser Glu Leu Ala Ala Ala Lys Leu Ala Gln Met
                125                 130                 135

CGG CCG CTG TGG AAG CCC GGG ACC GCC TTC GGG TAC CAC GCC CTG ACC        666
Arg Pro Leu Trp Lys Pro Gly Thr Ala Phe Gly Tyr His Ala Leu Thr
            140                 145                 150

ATC GGC GTC TTC ATG GAG GAG CTT TGC CGC CGG ATC ACC GGG TCC ACG        714
Ile Gly Val Phe Met Glu Glu Leu Cys Arg Arg Ile Thr Gly Ser Thr
                155                 160                 165

CTC CAG GAA ATC TAC GAA CAG CGG ATC CGC TCG GTC ACG GGC GCC CAC        762
Leu Gln Glu Ile Tyr Glu Gln Arg Ile Arg Ser Val Thr Gly Ala His
            170                 175                 180

TTC TTC CTG GGA CTG CCT GAG TCC GAG GAA CCC CGC TAT GCC ACC CTC        810
Phe Phe Leu Gly Leu Pro Glu Ser Glu Glu Pro Arg Tyr Ala Thr Leu
185                 190                 195                 200

CGT TGG GCT GCA GAC CCC TCC CAG CCG TGG ATT GAT CCC GCC AGC CAT        858
Arg Trp Ala Ala Asp Pro Ser Gln Pro Trp Ile Asp Pro Ala Ser His
                205                 210                 215

TTC GGC CTT TCC GCA AAC TCG GCC GTG GGG GAC ATC CTT GAC CTG CCC        906
Phe Gly Leu Ser Ala Asn Ser Ala Val Gly Asp Ile Leu Asp Leu Pro
            220                 225                 230

AAC CTC CGC GAG GTC CGC GCA GCC GGC CTG AGT TCA GCC GCC GGA GTC        954
Asn Leu Arg Glu Val Arg Ala Ala Gly Leu Ser Ser Ala Ala Gly Val
                235                 240                 245

GCC AGC GCG GAA GGC ATG GCC CGC GTC TAC GCT GCG GCA CTC ACC GGA       1002
Ala Ser Ala Glu Gly Met Ala Arg Val Tyr Ala Ala Ala Leu Thr Gly
            250                 255                 260
```

FIG.1(b)

```
CTT GCC GCC AAC GGC GAC CGA GCC GCC GTC GCG CCC CTC CTC AGC GAA    1050
Leu Ala Ala Asn Gly Asp Arg Ala Ala Val Ala Pro Leu Leu Ser Glu
265             270             275             280

GAG ACC ATC CAA ACC GTC ACG GCC GAG CAG GTC TTC GGC ATC GAC CGG    1098
Glu Thr Ile Gln Thr Val Thr Ala Glu Gln Val Phe Gly Ile Asp Arg
            285             290             295

GTG TTC GGC GAG ACG AGC TGC TTT GGG ACA GTG TTC ATG AAA TCG CAT    1146
Val Phe Gly Glu Thr Ser Cys Phe Gly Thr Val Phe Met Lys Ser His
        300             305             310

GCA CGC TCG CCT TAT GGC AGC TAC CGG GCG TTC GGG CAC GAC GGC GCC    1194
Ala Arg Ser Pro Tyr Gly Ser Tyr Arg Ala Phe Gly His Asp Gly Ala
            315             320             325

AGC GCA TCT TTG GGG TTC GCT GAC CCT GTG TAT GAA CTC GCC TTC GGG    1242
Ser Ala Ser Leu Gly Phe Ala Asp Pro Val Tyr Glu Leu Ala Phe Gly
        330             335             340

TAC GTG CCG CAA CAG GCC GAG CCG GGC GGA GCG GGA TGC CGC AAC CTT    1290
Tyr Val Pro Gln Gln Ala Glu Pro Gly Gly Ala Gly Cys Arg Asn Leu
345             350             355             360

GAG CTG AGC GCC GCC GTG CGG AAG GCA GTC ACC GAA CTG GCT CAG        1335
Glu Leu Ser Ala Ala Val Arg Lys Ala Val Thr Glu Leu Ala Gln
            365             370             375

TAGGATGAAG CATGACCGAA CCGAGATTCA CCGTTGAAAC AGCCATGGTC CTTGCCGAAG  1395
TGGCGCACAA TCGCCAGAAG GACAAGCTGA AGCGGCCGTA CCGCGAGCAC GTTCTGGCGG  1455
TAGGGGATGC GCTCGCCGAC TTCGACGACG ACATCCGGAT CGCAGGTTAC CTGCACGACA  1515
TCGCCAAGGA CACGCCGATT ACCAAGCAGG CGCTGCTCGA CATGGGTGTT TCCGAGCGTG  1575
CCGTGGGCAT CATCGAACGC GTGACGCGCC GATTCCAGGA TGATTCGGAC AACGATGAAG  1635
CCGTCGTTCT GCATATCGCA CAGGACCATG ACGCCACCCT GGTCAAGATC GCCTGCAACG  1695
```

```
CCCACAACTC CGTGCCGGAG CGCGTGCGGG CGCTCGCCGA AAAGTGGCCG GACAAGGCAC   1755
CCAGCACGCG CTACGCAGAC GCCCGGGAAG TGCTCTACAA GGCGGTGCCA CGGGGTGAAA   1815
TCCACTTGGT CCTGCAACGC ATCAACCCTG ATCTGCTGTC CGAGATGGAC CGGCTGGCGG   1875
ACTAGTAGTT CGACGCGGCA GGTCTCGCCT GTCTACGGTT TCGTCGGTTC GTCCTGAATC   1935
GGGTTGGCAG CGGCCGCCGC CTCCCGGGTA GCGGATGCGG TGACGTCCGC GAGAATCCGT   1995
TGGTGGATCT GGGCGGTGAG CTCGTGAATC GCACGCGTCA GGTCGGTGTT CTCCTCGAGC   2055
AGATGCTCCT GGGCGTTGTA GTCATGGTCT GCCTTCACCT GCTGGAAAGC CGCCTGACGG   2115
TTCTGTCCGA TCATGACGAA GGTCGAGAGG AAGATCGCTT CGAGCGAGAC GATCAAGGT    2175
```

GENE ENCODING ASYMMETRICALLY ACTIVE ESTERASE

This invention relates to an isolated gene encoding an esterase originating from a microorganism. More particularly, it relates to an isolated gene (or an isolated DNA) encoding an esterase useful for asymmetric hydrolysis, expression plasmids containing said DNA, microorganisms transformed with said expression plasmids, and the production of the esterase by culturing said transformants.

The recombinant esterase obtained according to the present invention can be used for the preparation of an optically active compound useful as an intermediate for clinically or agriculturally important substances. Examples of optically active compounds which can be produced by means of the esterase of the invention include an optically active chrysanthemic acid (KCA; 2,2-dimethyl-3-isobutenylcyclopropane-1-carboxylic acid), i.e., (+)-trans-KCA, useful as an acidic part for the production of pyrethroid insecticides.

Medically and/or agriculturally useful compounds, as well as their intermediates, often show complicated structure, which leads to the hardness of synthesis thereof by conventional organic synthetic methods. It should be more difficult when the desired compound is optically active. For example, pyrethrins, which can be produced from KCA, possess three asymmetric carbons and their insecticidal activity varies from one stereoisomer to another. Therefore, it has been needed to establish methods for preparing KCA or KCA derivatives of a desired structure for the preparation of desired stereoisomers of pyrethrins. However, the complexity of the structure prevented the development of such methods.

Recently, a bioreactor-system which utilizes an enzyme derived from organisms as a catalyst has been developed. This system takes advantage of the rigid stereospecificity of enzymes. Examples of enzymes employed in such reactions include an esterase derived from pig liver (Laumen et al, Tetrahedron Lett. 26:407–410 (1985); and Wang et al (J.Am. Chem. Soc. 106: 3695 (1984)). Microorganism-derived enzymes have also been used for the same purpose. For example, an esterase derived from Bacillus subtilis NRRL-B-558 was used for the synthesis of cephalosporin derivatives (Appl Microbiol. 30:413–419 (1975)). However, the isolation and purification of enzymes from an organism in sufficient amounts is not easy. Furthermore, the enzymes derived from mammalian tissue are usually unstable (like PLE), hard to handle and uneconomical because of the limited supply, and therefore are often unsuitable for industrial application. When an organism-derived hydrolytic enzyme such as esterase, lipase or the like is used as a bioreactor for the production of an optically active compound, it can catalyze the following illustrative reactions: (a) stereoselective hydrolysis of a racemic compound; (b) site selective hydrolysis of a pro-chiral compound which gives rise to a chiral compound; or (c) stereoselective ester-formation as the reverse reaction of the above (a) or (b).

In order to apply a microorganism-derived esterase to the stereoselective hydrolysis of a racemic ester, it is necessary to search a lot of naturally occurring microorganisms to select a particular strain capable of producing a desired enzyme with a high specific activity, culture the same, and isolate and purify the produced enzyme, if desired. However, these processes generally involve many problems such as difficulty in cultivation, inadequate activity, poor efficiency, low productivity and the like. These facts made it difficult to proceed with the industrial production of an optically active compound by means of a cultured microorganism or a purified enzyme therefrom. Thus, it has been needed to obtain sufficient amounts of an esterase broadly employable for the organic synthesis of optically active compounds such as KCA. In this regard, bacterial esterases are especially useful because many kinds of biologically active enzymes can be synthesized by means of recombinant DNA technology using bacterial cells as hosts.

The present inventors, under these circumstances, had searched various microorganisms and have found that a strain of Arthrobacter globiformis, designated as IFO-12958, produces an esterase having a high stereoselectivity to various kinds of substrates and disclosed (Japanese Patent Publication (KOKAI) No. 181788/1989). However, owing to the low expression of the esterase, A. globiformis IFO-12958 could not give sufficient hydrolytic effeciency and was not suited for industrial application. In the course of further investigation, the inventors isolated the gene encoding the esterase from SC-6-98-28 (FERM BP-3658), which produces the esterase with an excellent property.

In order to establish the production of an esterase having stereoselective activity by means of recombinant DNA technology, the inventors have isolated and purified a peptide having esterase activity from SC-6-98-28, cloned said gene and determined the nucleotide sequence of the gene encoding the esterase.

For the purpose of the invention as is herein disclosed, when the term "gene" or "DNA" are used to express a structural gene or DNA encoding an esterase, it means an isolated gene or DNA encoding esterase originated from A. globiformis SC-6-98-28.

The DNA of the invention can be transformed into a host cell such as a procaryotic cell to obtain a transformant capable of producing a recombinant esterase abundantly. The transformed cells, when cultured in an appropriate medium, give a culture broth having a significantly elevated catalytic activity of the esterase. The thus obtained culture broth or processed material thereof, or purified esterase therefrom can be used as a bioreactor in the asymmetric hydrolysis of a precursor compound to give a compound having a desired structure.

Once the gene has been identified and cloned, the preparation of microorganisms capable of producing the esterase and the production of said esterase can be easily accomplished using known recombinant DNA technology, which comprises, for example, constructing expression plasmids encoding said gene and transforming a microorganism with said expression plasmids, cultivating the transformant in a medium under suitable conditions for the expression of the esterase, and isolating the product having the esterase activity, if desired.

Thus, the first object of the invention is to provide an isolated gene encoding an esterase capable of catalyzing a stereoselective hydrolysis.

The gene of the invention preferably encodes an amino acid sequence shown by the SEQ ID No.1 in the accompanying Sequence Listing, more preferably, it has the nucleotide sequence shown by the SEQ ID No.2.

The esterase-encoding gene of the invention can be obtained from a microorganism which produces a desired esterase such as A. globiformis SC-6-98-28. Thus, the cloning of a gene can be accomplished by constructing a genomic library from total DNA obtained from chromosomal DNA of a microorganism such as *A. globiformis* SC-6-98-28 according to a conventional technique, probing said library, and cloning a DNA encoding esterase as will be further explained below. In the illustrative example, the cloning was carried out conventionally by preparing a genomic library by isolating chromosomal DNA from SC-6-98-28, digesting the total DNA with a restriction enzyme and cloning the obtained fragments into the phage vector λgt11 or the plasmid vector pUC19, transfecting the phage or transforming the competent *E. coli* JM cells with the mixture of the cloned fragments, and screening the plaques or colonies obtained.

Selection of DNA can be conducted by any of the known methods such as immunometric assay using anti-esterase antibody, hybridization using synthetic DNA probes corresponding to partial amino acid sequences of a purified peptide, or screening the clones on the basis of the esterase activity. When only a part of the DNA fragment encoding the esterase is obtained, the remaining part of DNA, and consequently the full length of the esterase encoding DNA, can be obtained using said fragment as a probe. In the following Example, a part of a positive clone pK-12 was used for screening pEH16, which was followed by the construction of a clone pAGE-1 encoding the entire coding region of the esterase. The thus obtained gene preferably contains a nucleotide sequence encoding an amino acid sequence shown by the SEQ ID No.1. More preferably, the gene has the nucleotide sequence shown by the SEQ ID No.2.

The DNA encoding the esterase is then used to construct expression plasmids which enable a microorganism to produce the esterase using the known recombinant technology.

Thus, the second object of the invention is to provide expression plasmids containing a nucleotide sequence encoding an esterase.

Preferably, expression vectors which can be used in the invention contain sequences necessary for their replication in a host cell and are autonomously replicable. It is also preferable that the vectors contain selectable marker(s) and can be easily selected from the untransformed cells. Many vectors and restriction enzymes used for the digestion of given DNA are obtainable from commercial sources and the operations are well-known to those skilled in the art. For the purposes of the invention, it is preferable to use vectors functional in *E. coli*. Although it is in no way limited to the use of a particular vector, for the expression in *E. coli*, vectors containing promoters such as lac, tac, trp and the like are preferable. Such expression vectors are conveniently obtained as promoter cartridges from Pharmacia PL, Inc. Examples of especially preferred expression plasmids of the invention are PAGE-201, PAGE-202 and PAGE-203 which contain the gene shown by the above-mentioned nucleotide sequence.

The third object of the invention is to provide a microorganism transformed by an expression plasmid of the invention and capable of producing an esterase having the above-mentioned activity. Examples of suitable host cells include various eucaryotic and procaryotic cells such as *E. coli*, *Bacillus subtilis*, lactic acid bacterium and fungi. The preferred host cell is *E. coli*. Examples of preferred microorganisms are *Escherichia coli* JM109 (PAGE-201), *E. coli* JM109 (PAGE-202), *E. coli* JM109 (PAGE-203), *E. coli* JM105 (PAGE-201), *E. coli* JM105 (PAGE-202) and *E. coli* JM105 (PAGE-203). The host cell can be transformed with an expression plasmid of the invention and cultivated using any of the well known procedures in the art to give a cultured broth comprising esterase-producing cells. In the working example as mentioned below, illustrative expression plasmids pAGE-201, 202 and 203 containing the DNA encoding esterase under the control of tac promotor were constructed and used to transform *E. coli* JM109 or JM105. The resultant transformants expressed products having esterase activity to a high extent after cultivation. The cultured broth containing the esterase activity is then subjected to centrifugation or filtration to separate the supernatant.

*E. coli* host cells harboring the expression plasmids of the invention were grown in M9 medium at 37° C. using IPTG as an inducer. A part of the harvested cells, when assayed by SDS-PAGE, gave a main band at 40,000, showing that the cell expressed the desired esterase abundantly.

The esterase activity usually exists in the transformed cell and therefore cells separated from the cultured broth by filtration or centrifugation can be used in the hydrolytic reactions. However, preparations which are usually obtained from the cultured cells in conventional manners are also useful. Examples of such preparations include dried cells, cell-free extract, enzyme solution, immobilized cells or enzyme using an appropriate solid support.

Thus, the present invention further provides a method for preparing an esterase by culturing a transformant of the invention in an aqueous nutrient medium containing assimilable carbon or nitrogen sources under aerobic conditions.

When the resultant preparations are used for the asymmetric hydrolysis, the preparation is contacted with a compound to be hydrolysed to give an optically active stereoisomer useful in the pharmaceutical and/or agricultural fields. In the following Examples, an racemic ethyl ester of KCA (referred to as KCE) was hydrolyzed to give (+)-trans KCA exclusively, which is useful as an intermediate for the production of effective pyrethroid insecticides. According to the present invention, it is possible to produce plenty of esterase useful as a bioreactor by culturing transformants.

Following Examples further illustrate and detail the invention disclosed, but should not be construed to limit the invention.

EXAMPLE 1

Isolation of DNA Clone Encoding an Esterase

1. Preparation of Chromosomal DNA

*Arthrobacter globiformis* SC-6-98-28 strain (FERM P-11851) was pre-cultivated in a 5 ml medium (3.0% soluble starch, 0.7% polypeptone, 0.5% yeast extract, 0.5% $KH_2PO_4$, pH 5.0) for 24 hr at 30° C. with shaking. The culture was inoculated into 500 ml of growth medium (6.0% soluble starch, 1.0% polypeptone, 0.2% yeast extract, 0.5% $KH_2PO_4$, pH 5.0) and grown at 30° C. with shaking until the absorbance at 660 nm ($OD_{660}$) reached 0.25, where penicillin G was added to the final concentration of 300 units/ml culture and the cultivation was continued until the $OD_{660}$ reached 1.0. Cells were harvested by centrifugation and suspended into 45 ml of a mixture of 150 mM NaCl, 15 mM sodium citrate, 10 mM EDTA and 27% sucrose, and egg lysozyme was added to a final concentration of 5 mg/ml. The mixture was incubated at 37° C. for 30 min and 10 ml of 10% SDS was added thereto. After the addition of protease K to a final concentration of 200 μg/ml, the incubation was continued at 37° C. for 4 hr. The culture was extracted with an equal volume of 0.1M Tris-saturated phenol (x2) and ether (x2). DNA was precipitated from the aqueous layer by adding 2 volumes of ethanol and recovered by winding threads of DNA on a glass rod. After drying, the recovered nucleic acids were dissolved into 5 ml Tris-EDTA (10 mM Tris-HCl, pH 8.0 and 1 mM EDTA) and treated with RNase at the final concentration of 100 μg/ml at 37° C. for 2 hr. The mixture was extracted with an equal volume of phenol-chloroform (1:1 in volume) (x2) and DNA was precipitated from the aqueous layer by the addition of 2 volumes of cold ethanol. The resultant DNA was washed with 80% ethanol, dried and dissolved into Tris-EDTA buffer. About 5.8 mg of chromosomal DNA was obtained.

2. Screening of Genomic Library

Chromosomal DNA obtained in the above 1. was digested with KpnI. vector pUC 19 (Takara Shuzo, Japan) was digested with KpnI and treated with alkaline phosphatase. The KpnI-digested DNA fragments were ligated into the KpnI site of pUC 19 using T4 DNA ligase and the ligation mixture was transformed into a competent *E. coli* K-12 JM109 (Takara Shuzo, Japan). When the *E. coli* JM109 cells containing pUC 19 are grown on LB-agar medium containing ampicillin, IPTG and X-Gal, wild type colonies give blue color as the result of the cleavage of X-Gal by β-galactosidase produced in the JM 109 cells. However, the transformed *E. coli* JM109 cells which have a foreign DNA fragment inserted into the multi-cloning site of pUC 19 are colorless grown under the same conditions because the transformants lack the ability to express the galactosidase activity.

Thus, white colonies were selected on the plate and subjected to colony hybridization using synthesized DNA probes corresponding to N-terminal amino acid sequence of a purified esterase. The white colonies were spread on a plate and transferred onto a nylon membrane conventionally, or inoculated onto the membrane with bamboo spits. The membrane was placed on a LB-ampicillin plate and incubated at 37° C. for several hours until colonies appeared on the membrane. DNA was extracted from the colonies by soaking (x2) the membrane in 0.5N NaOH to lyse cells, and washing (x2) the membrane with 1M Tris-HCl (pH 7.5) for neutralization. DNA was then fixed onto the membrane by drying at 80° C. under vacuum for 2 hr.

The membrane was treated at 55° C. for 1 hr in a mixture (A) comprising 6x SSC, 10 x Denhardt's reagent (0.2% Ficol, 0.2% polyvinylpyrrolidone, 0.2% bovine serum albumin) and then at 55° C. for 4 hr in a mixture (B) comprising 6x SSC, 1% SDS, 10 x Denhardt's reagent, 100 μg/ml denatured salmon sperm DNA. The hybridization was performed at 55° C. overnight in a plastic bag containing the membranes, the above mixture (B) and radiolabeled probes ($5 \times 10^5$ cpm/membrane) prepared by labeling the DNA mixture at the 5' terminus with [$\gamma^{32}P$] ATP and purifying by a column chromatography. After hybridization, the membranes were washed sequentially (1) at 55° C. for 15 min in 6x SSC, (2) at 55° C. for 30 min in 6x SSC, (3) at 55° C. for 30 min in 6x SSC plus 1% SDS. The membranes were air-dried and autoradiogramed by exposing to X-ray film (FUJI RX) with an intensifying screen. A positive clone pK-12 strain was separated.

Figure 1:
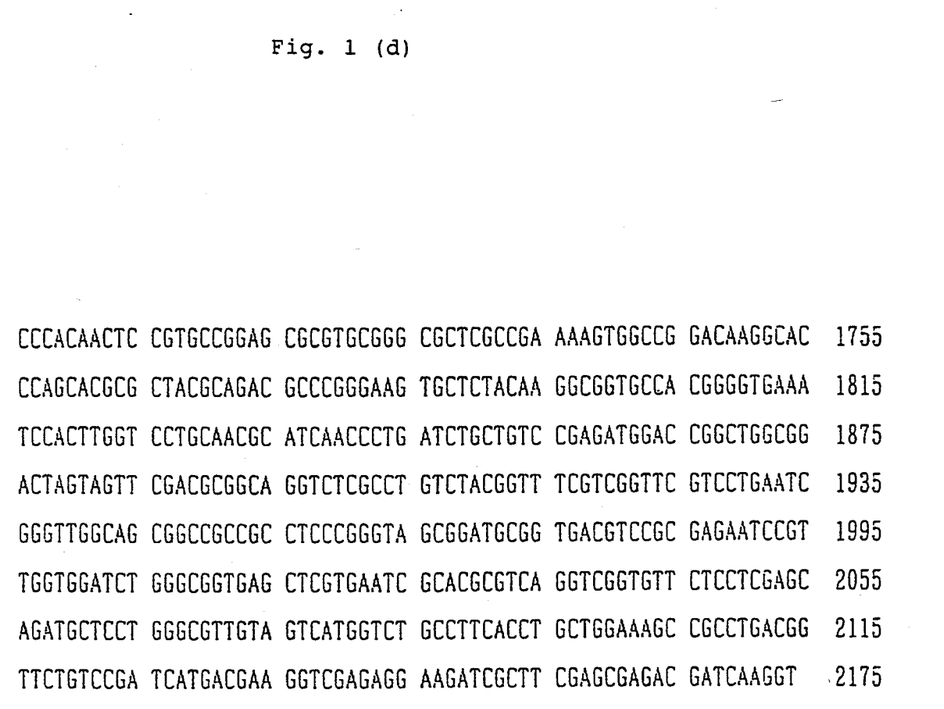
FIGS. 1A–1D show a deduced amino acid sequence of an entire 2,174 bp DNA insert in plasmid PAGE-1. The DNA sequence contains a translational region encoding esterase (nucleotides 211–1335) and the N-terminal sequence used as a DNA probe for the screening (nucleotides 211–230).
Figure 1A:
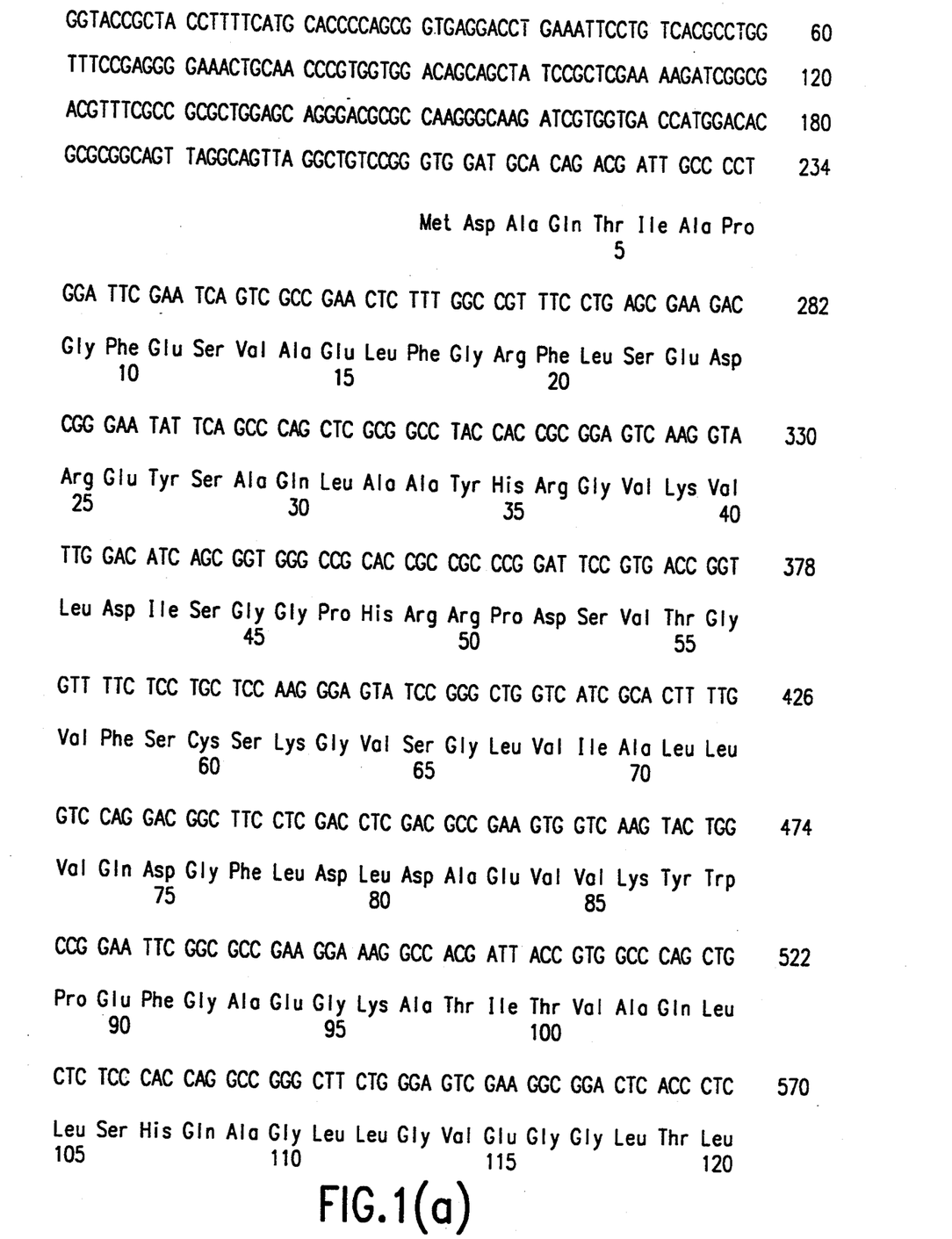
Figure 1B:
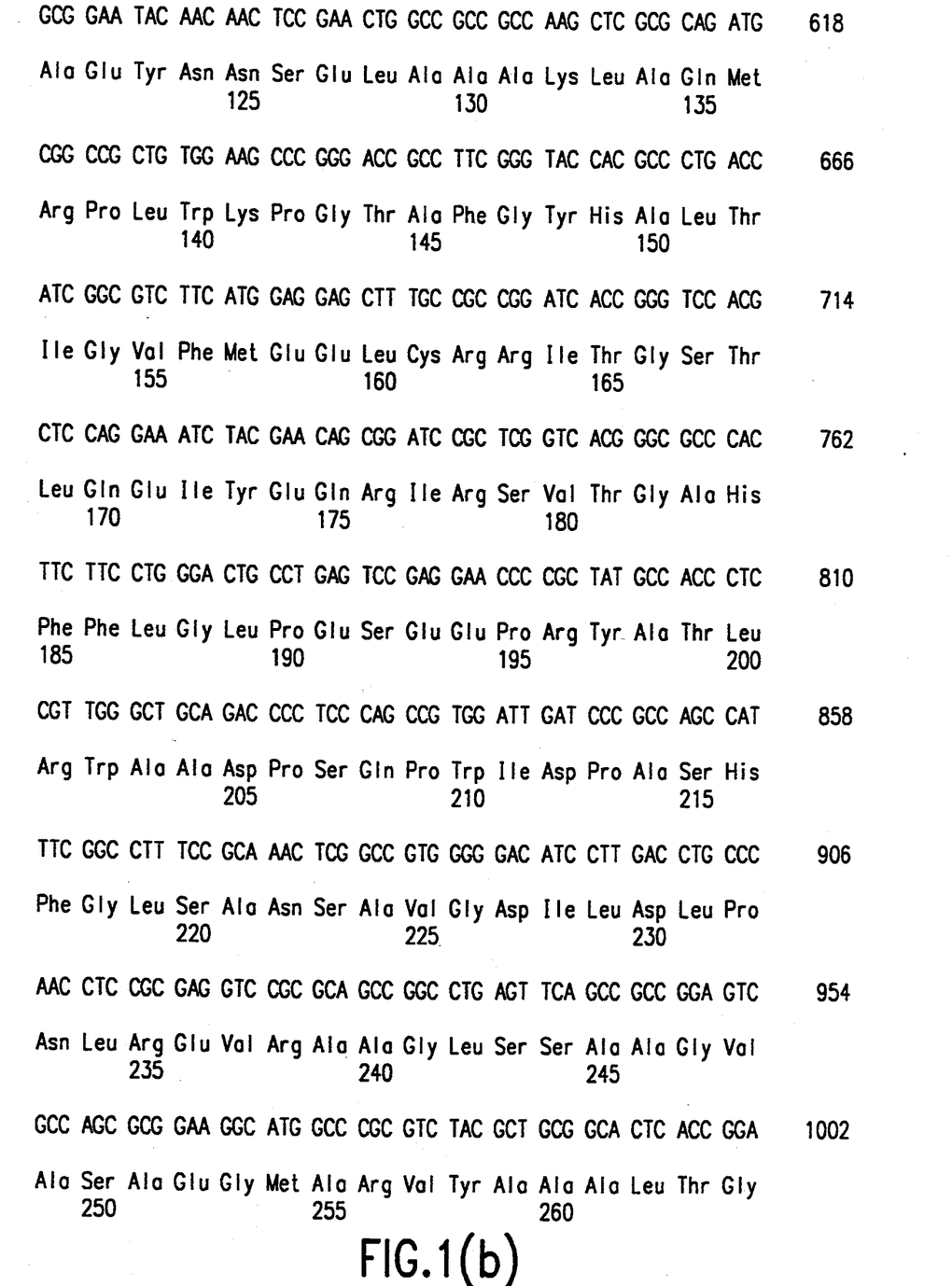
Figure 1C:
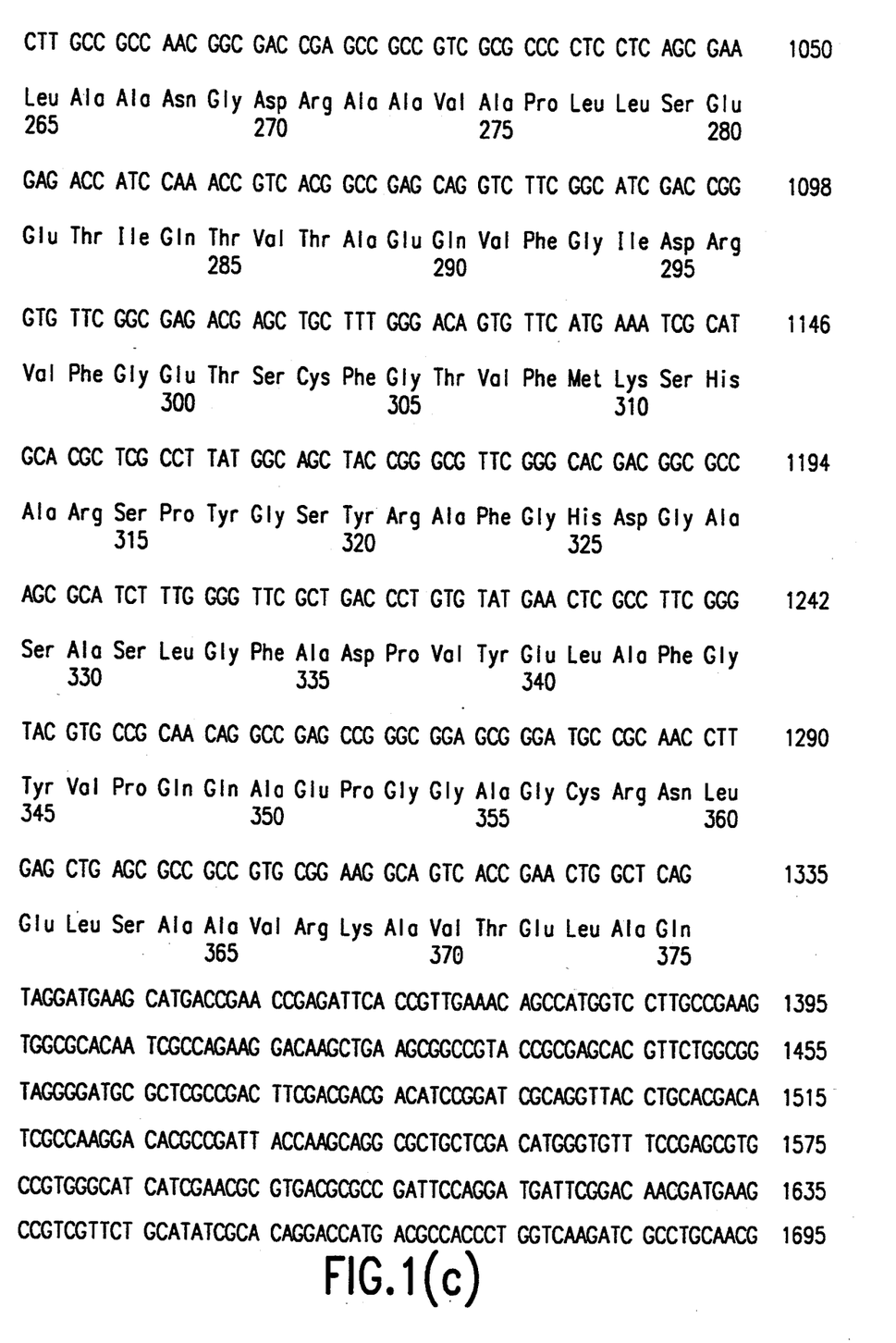
Figure 2:
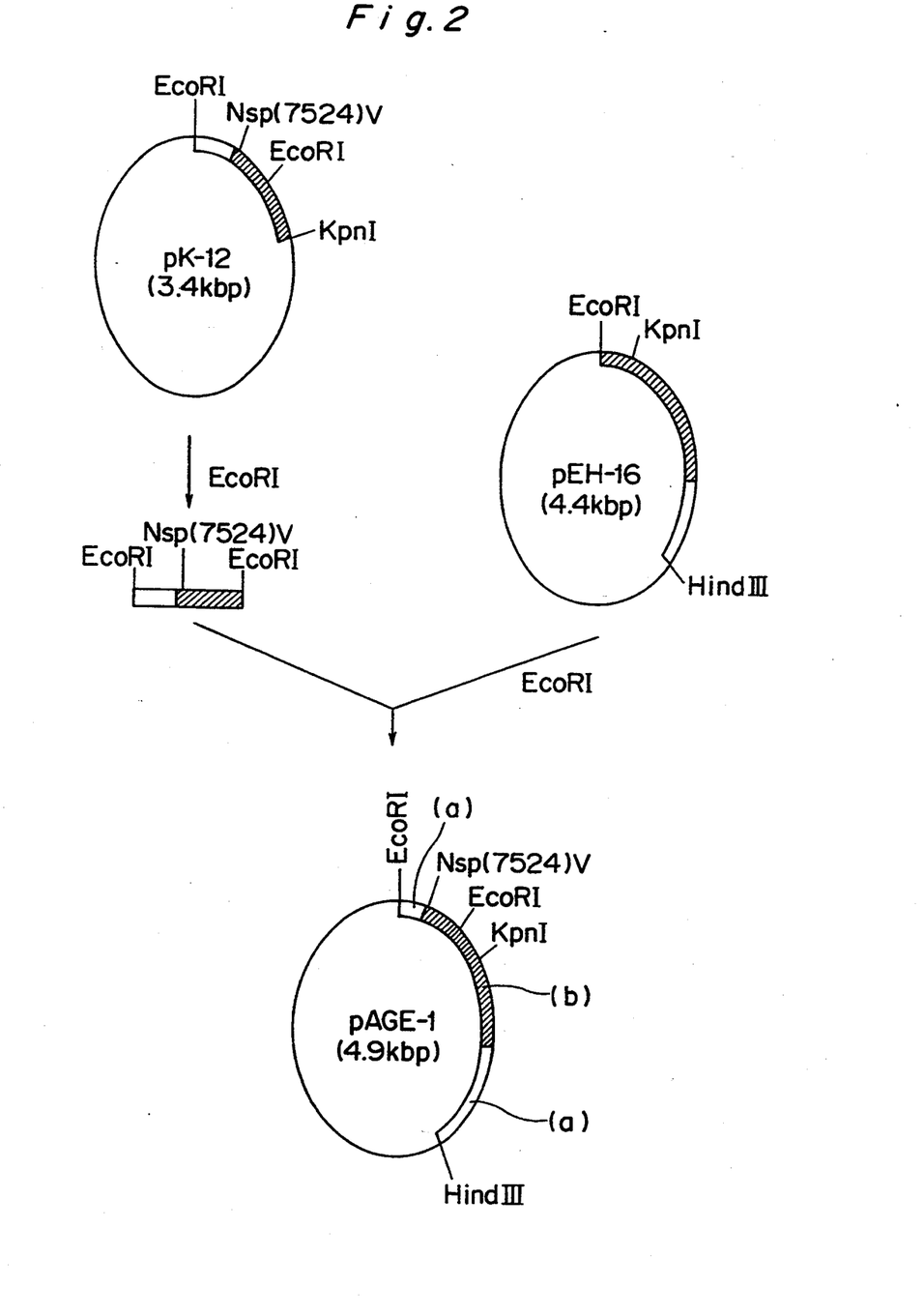
FIG. 2 shows the positive clones PK-12 and pEH16 obtained by colony hybridization and a restriction map of plasmid PAGE-1 constructed from these clones, which contains (a) a DNA originated from *A. globiformis* and (b) the entire coding region of the esterase.
Figure 3:
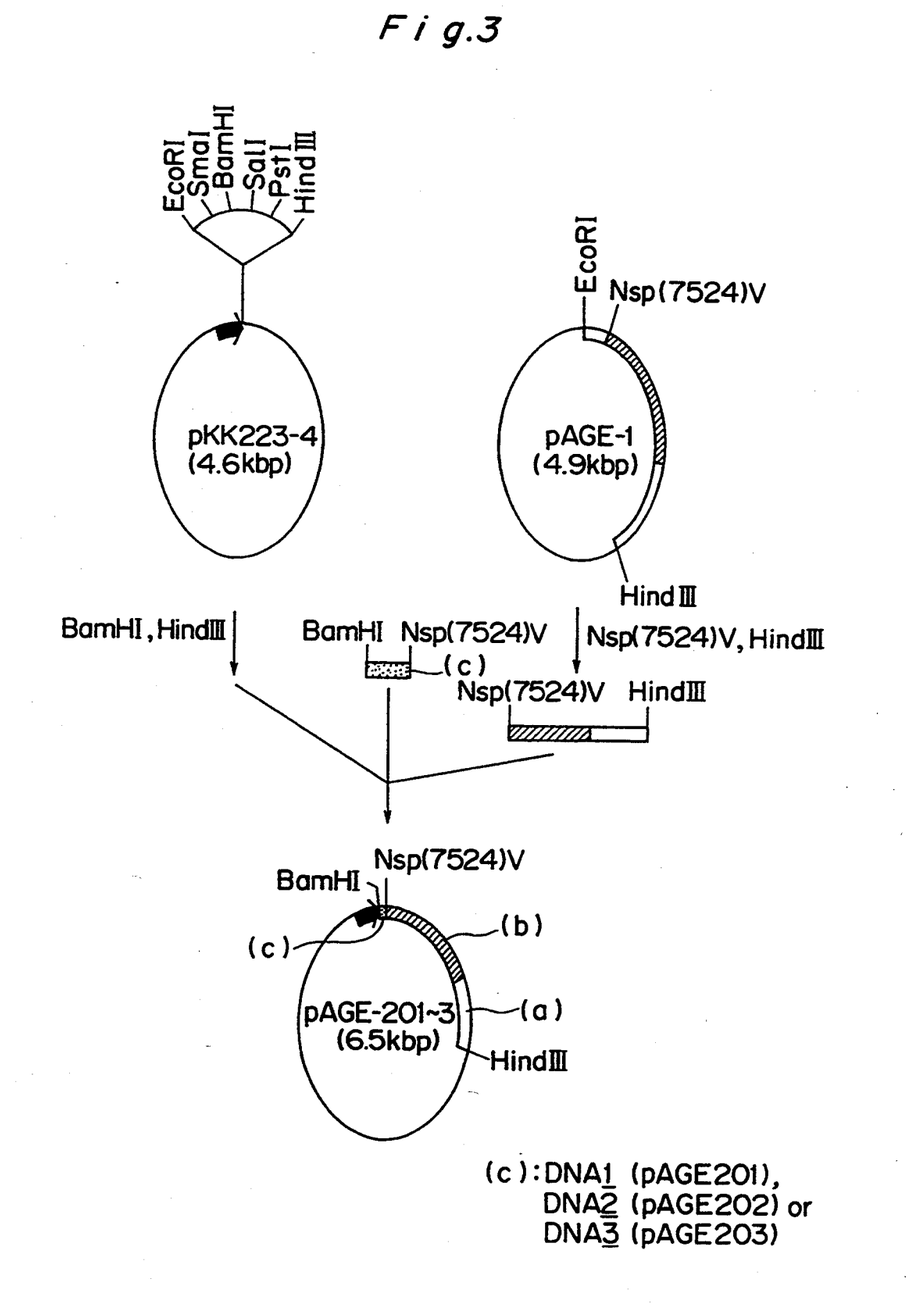
FIG. 3 shows a construction strategy of the esterase expression plasmids pAGE-201, pAGE-202, and pAGE-203. Each plasmid contains a synthetic DNA (c) (1, 2, and 3) and a tac promoter (bold arrow).

The clone pK-12 was not long enough to encode the entire esterase. The nucleotide sequence of pK-12 was determined by the dideoxy method and a part of the sequence was used to probe a DNA library prepared by digesting chromosomal DNA with EcoRI and ligating the fragments to EcoRI-digested vector pUC19. By the colony hybridization, a positive clone pEH-16 was isolated. Plasmid pAGE-1, containing the whole translational region encoding esterase, was constructed by removing an EcoRI fragment from pK-12 and ligating said fragment to the EcoRI site of pEH-16. The construction of plasmid pAGE-1 is shown in FIG. 2.

3. Sequence Analysis of Esterase Gene and Construction of Restriction Map

A restriction map of the cloned DNA obtained in the above 2. was prepared as follows.

*E. coli* JM109 each transformed with plasmid pK1 and pEH16 was grown and plasmid DNA was prepared according to the method of Birnboim-Doly. Plasmid DNA was digested with various restriction enzymes and the length of each DNA fragment was determined by 1% agarose gel electrophoresis and 5% polyacrylamide gel electrophoresis. Comparing the length of strands of resultant DNA fragments, a restriction map was completed.

4. Determination of Nucleotide Sequence of DNA Encoding Esterase and Deduced Amino Acid Sequence The sequence of 2,175 base pairs of the insert in the plasmid pAGE-1 was determined by the dideoxy method using the forward and reverse primer DNAs (Takara Shuzo) for pUC plasmid, successively synthesized primer DNAs and 7-deaza sequencing kit (Takara Shuzo). The over all 2,174 bp nucleotide sequence of an insert in pAGE-1 is provided in FIG. 1 and Sequence Listing (SEQ ID No.2). An investigation of the base sequence revealed that there is a unique open-reading frame (nucleotide 211 (in GTG) to 1335). Additionally, the amino acid sequence encoded by the nucleotide sequence down stream of the possible translational initiation codon of said frame is consistent with that of the N-terminal sequence of the purified esterase peptide, which demonstrates that said region of the sequence is the open reading frame encoding the esterase. Thus, the esterase was proved to be a protein of a molecular weight of 39,839 composed of 375 amino acid residues. The deduced amino acid sequence is also provided in FIG. 1 and Sequence Listing (SEQ ID No.1).

EXAMPLE 3

Construction of Expression Plasmids for Esterase

Plasmid pKK223-4 was prepared by deleting one BamHI restriction site from an expression vector pKK223-3 (Boyer et al, Proc. Natl. Acad Sci. USA, 80: 21-25 (1983); Farmacia). The pKK223-3 was partially digested with BamHI, blunted with T4 DNA polymerase and religated to give the desired plasmid pKK223-4.

To modify the upstream region of the translational initiation codon of the esterase gene, the following DNA fragments were synthesized using an Applied Biosystems DNA synthesizer (Model 380A).

| DNA fragment | Sequence identifier number |
|---|---|
| PH-22 | SEQ ID No. 3 |
| PH-21 | SEQ ID No. 4 |
| ES-01 | SEQ ID No. 5 |
| ES-02 | SEQ ID No. 6 |
| ES-13 | SEQ ID No. 7 |
| ES-11 | SEQ ID No. 8 |
| ES-12 | SEQ ID No. 9 |
| ES-21 | SEQ ID No. 10 |
| ES-22 | SEQ ID No. 11 |

Synthesized oligonucleotides fragments PH-21, ES-01, ES-11, ES-21, and ES-13 were 5'-end phosphorylated and subjected to the ligation and annealing with untreated fragments to give the following three double-stranded DNA fragments.

```
          PH-22                             ES-01                              1
GATCCTTTTTTAATAAAATC | AGGAGGTAAAA AACGATGGACGCACAGACCATCGCACCGGGCTT
     GAAAAAATTATTTTAG TCCTCCATTTT | TTGCTACCTGCGTGTCTGGTAGCGTGGCCCGAAGC
BamHI          PH-21                             ES-02              Nsp(7524)V

PH-22                             ES-11                              2
GATCCTTTTTTAATAAAATC | AGGAGGAAAAA ATCGATGGACGCACAGACCATCGCACCGGGCTT
     GAAAAAATTATTTTAG TCCTCCTTTTT | TAGCTACCTGCGTGTCTGGTAGCGTGGCCCGAAGC
BamHI          ES-13                             ES-12              Nsp(7524)V

PH-22                             ES-21                              3
GATCCTTTTTTAATAAAATC | AGGAGGAAAAA ATATGGACGCACAGACCATCGCACCGGGCTT
     GAAAAAATTATTTTAG TCCTCCTTTTT | TATACCTGCGTGTCTGGTAGCGTGGCCCGAAGC
BamHI          ES-13                             ES-22              Nsp(7524)V
```

The double-stranded DNA fragments were kinased at the both ends. An esterase coding region was isolated from plasmid pAGE-1 by the double digestion with restriction enzymes Nsp(7524) V and HindIII. A ligation reaction was carried out in a mixture containing the isolated esterase-encoding DNA fragment, synthesized DNA fragment and BamHI, HindIII-digested, alkaline phosphatase-treated vector pKK223-4. Thus, expression plasmids pAGE-201, 202 and 203 for transforming E. coli host cells, which contain down stream of a tac promoter a modified DNA Sequences 1, 2, and 3 and an esterase gene in this order, were obtained.

EXAMPLE 4

Preparation of Stereoselective Esterase

1. Growth of Transformants

The esterase capable of asymmetrically hydrolyzing a racemic ester of chrysanthemic acid (KCA) was produced by culturing E. coli JM109/pAGE-201, 202 or 203. E. coli JM109 was transformed with a expression plasmid prepared in Example 3 and cultured in a M9 medium (10.5 g $K_2HPO_4$, 4.5 g $KH_2PO_4$, 1.0 g $(NH_4)_2SO_4$, 0.5 g sodium citrate, 0.2 g $MgSO_4$ $7H_2O$, 2.0 g glucose, 2 mg/ml thiamine HCl) at 37° C. to a logarithmic phase, where IPTG (isopropyl thio-β-D-galactoside ) was added to a final concentration of 1 mM to induce the expression of the esterase.

Cells were harvested by centrifugation. SDS-PAGE analysis conducted using a portion of cells gave a main band at molecular weight of 40,000 demonstrating that the esterase was expressed to a high extent in the E. coli transformed by either of the plasmids pAGE-201, 202 or 203.

2. Asymmetric Hydrolysis of a Racemic Ethyl Ester by Recombinant E. coli JM109 Cells The E. coli cells transformed with plasmid pAGE-201, 202 or 203 were evaluated as to the effect on the asymmetric hydrolysis of a racemic ethyl ester (referred to as KCE) of chrysanthemic acid (cis:trans=10:90; (+):(−)=50:50). E. coli JM109/pAGE-201,202 or 203 cells obtained from 100 ml culture were suspended into 50 ml of 200 mM glycine/sodium hydroxide buffer (pH 10.0). To the suspension was added 1.0 g of KCE and reacted at 37° C. with stirring at 1,000 rpm for 6 hr and the reaction stopped by the addition of 5.0 ml of 35% HCl. The resultant KCA product and unreacted KCE were extracted with methyl isobutyl ketone (MIBK) from the acidic mixture. The extract was analyzed by gas chromatography (column: Shinchrom $F_{51}+H_3po_4$ (10+1%), 2.6 m, 190° C.) and the hydrolytic effeciency was calculated according to area percentage.

To the organic extract was added 20 ml of 0.01N NaOH and the KCA only was extracted into the aqueous layer as a sodium salt. The aqueous solution was again treated with 35% HCl and KCA was extracted with MIBK. The extract was concentrated and dehydrated. The content of the four isomers of KCA was analyzed as follows. A portion of the extract was mixed with dicyclohexylcarbodiimide and 3,5-dichloroaniline and allowed to stand for 3 hr at room temperature, which was followed by the analysis by a high-performance liquid chromatography (column: SUMIPAX OA-2100×2; mobile phase: n-hexane/1,2-dichloromethane (17:3, v/v); flow rate: 1.5 ml/min, detection: 254 nm). Results are given in Table 1 below.

TABLE 1

| Strain | hydrolytic effeciency[1] (%) | cis/trans ratio (%) (+)- (−) (+)- (−)- cis:-cis:trans:trans |
|---|---|---|
| JM109/pAGE-201 | 96.3 | 0:0:100:0 |
| JM109/pAGE-202 | 100 | 0:0:100:0 |
| JM109/pAGE-203 | 89.1 | 0:0:100:0 |
| JM109 | 0 | |

[1]Hydrolytic effeciency: the amount of resultant (+)-trans KCA to the amount of (+)-trans KCE in the starting material.

3. Asymmetric Hydrolysis of a Racemic Ethyl Ester by Recombinant E. coli JM105 Cells Transformants producing esterase activity were prepared and evaluated in the same manner as above 2, except that E. coli JM105 was used as a host cell. E. coli JM105 cells were transformed with plasmids pAGE-201, 202 or 203 and grown in M9 medium at 37° C. by inducing the expression of esterase by the addition of IPTG to a final concentration of 1 mM at the logarithmic phase. Cells were harvested and used for hydrolysis of a racemic ethyl ester of KCE (cis:trans=10:90; (+):(−)=50:50) in the same manner as above 2. Hydrolytic effeciency was evaluated by the gas chromatography (column: Shinchrom $F_{51}+H_3PO_4$ (10+1%), 2.6 m, 190° C.). The hydrolytic effeciency was evaluated according to the area percentage. The content of four isomers of KCA was analyzed by HPLC in the same manner as above 2. Results are given in Table 2 below.

TABLE 2

| Strain | hydrolytic effeciency (%) | cis/trans ratio (%) (+)- (−)- (+)- (−)- cis:-cis:trans:trans |
|---|---|---|
| JM105/pAGE-201 | 55.9 | 0:0:100:0 |
| JM105/pAGE-202 | 92.9 | 0:0:100:0 |
| JMI05/pAGE-203 | 100 | 0:0:100:0 |

As is clear from the above Tables 1 and 2, the expression of esterase in transformants was extremely promoted by cloning the gene into E. coli cells and changing the promoter and upstream region to a suitable sequence for E. coli, whereby the asymmetric hydrolysis of the racemic compound was surprisingly improved. Thus, according to the present invention, desired (+)-trans KCA can be produced in high yield. When Arthrobacter globiformis IFO-12958, which expresses esterase slightly, was grown and 20 μg of a purified enzyme (corresponding to 2.5 L culture) was used for the hydrolysis of 90 KCE (concentration: 2 w/v %; temperature: 40° C.; reaction period: 24 hr), the hydrolytic effeciency was only 6.4% (Japanese Patent Publication (KOKAI) No. 181788/1989).

What we claim is:

1. An isolated gene encoding an esterase capable of asymmetrically hydrolysing a racemic ester of chrysanthemic acid or its derivatives to produce (+)-trans acid having 100% optical purity, wherein said gene encodes an amino acid sequence presented in the SEQ ID No. 1 and which gene originated from *Arthrobacter globiformis* SC-6-98-28.

2. The gene according to claim 1 wherein said gene encodes the nucleotide sequence presented in SEQ ID No.2.

3. A plasmid which contains a gene of claim 2.

4. Plasmid pAGE-201.

5. Plasmid pAGE-202.

6. Plasmid pAGE-203.

7. A microorganism transformed by a plasmid of claim 3.

8. The microorganism of claim 7 which is *Escherichia coli*.

9. The microorganism of claim 7 which is *Escherichia coli* JM109.

10. *E. coli* JM109/pAGE-201.

11. *E. coli* JM109/pAGE-202.

12. *E. coli* JM109/pAGE-203.

13. The microorganism of claim 7 which is *Escherichia coli* JM105.

14. *E. coli* JM105/pAGE-201.

15. *E. coli* JM105/pAGE-202.

16. *E. coli* JM105/pAGE-203.

17. Method of hydrolysing a racemic ester of chrysanthemic acid or its derivatives to produce (+)-trans acid having 100% optical purity, which comprises contacting the transformed microorganisms of claim 8, 9, 11, 12, 13, 14, 15 or 16, or esterase purified from a culture obtained from the above transformed microorganism with the ester to be hydrolyzed.

18. Method of expression of an esterase asymmetrically hydrolysing a racemic ester of chrysanthemic acid or its derivatives to produce (+)-trans acid having 100% optical purity, which comprises transforming a microorganism with the plasmid of claim 3, 4, 5 or 6 to induce the expression of the esterase.

19. Method for constructing a plasmid, which comprises inserting the isolated gene of claim 1 or 2 in an expression plasmid to transform a microorganism with the plasmid.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 375 amino acids
        ( B ) TYPE: amino acid
        ( C ) STRANDEDNESS: single
        ( D ) TOPOLOGY: linear     ( i i ) MOLECULE TYPE: protein     ( v i ) ORIGINAL SOURCE:
        ( A ) ORGANISM: Arthrobacter globiformis
        ( B ) STRAIN: SC-6-98-28 (Ferm BP- 3618)

( x i ) SEQUENCE DESCRIPTION: SEQ ID NO:1:

```
Met Asp Ala Gln Thr Ile Ala Pro Gly Phe Glu Ser Val Ala Glu
 1               5                  10                  15

Leu Phe Gly Arg Phe Leu Ser Glu Asp Arg Glu Tyr Ser Ala Gln
                20                  25                  30

Leu Ala Ala Tyr His Arg Gly Val Lys Val Leu Asp Ile Ser Gly
                35                  40                  45

Gly Pro His Arg Arg Pro Asp Ser Val Thr Gly Val Phe Ser Cys
                50                  55                  60

Ser Lys Gly Val Ser Gly Leu Val Ile Ala Leu Leu Val Gln Asp
                65                  70                  75

Gly Phe Leu Asp Leu Asp Ala Glu Val Val Lys Tyr Trp Pro Glu
                80                  85                  90

Phe Gly Ala Glu Gly Lys Ala Thr Ile Thr Val Ala Gln Leu Leu
                95                      100                 105

Ser His Gln Ala Gly Leu Leu Gly Val Glu Gly Gly Leu Thr Leu
                110                 115                 120

Ala Glu Tyr Asn Asn Ser Glu Leu Ala Ala Ala Lys Leu Ala Gln
                125                 130                 135

Met Arg Pro Leu Trp Lys Pro Gly Thr Ala Phe Gly Tyr His Ala
                140                 145                 150
```

| | | | | | | | | | | | | | | |
|---|---|---|---|---|---|---|---|---|---|---|---|---|---|---|
| Leu | Thr | Ile | Gly | Val | Phe | Met | Glu | Glu | Leu | Cys | Arg | Arg | Ile | Thr |
| | | | | 155 | | | | 160 | | | | | | 165 |
| Gly | Ser | Thr | Leu | Gln | Glu | Ile | Tyr | Glu | Gln | Arg | Ile | Arg | Ser | Val |
| | | | | 170 | | | | 175 | | | | | | 180 |
| Thr | Gly | Ala | His | Phe | Phe | Leu | Gly | Leu | Pro | Glu | Ser | Glu | Glu | Pro |
| | | | | 185 | | | | 190 | | | | | | 195 |
| Arg | Tyr | Ala | Thr | Leu | Arg | Trp | Ala | Ala | Asp | Pro | Ser | Gln | Pro | Trp |
| | | | | 200 | | | | 205 | | | | | | 210 |
| Ile | Asp | Pro | Ala | Ser | His | Phe | Gly | Leu | Ser | Ala | Asn | Ser | Ala | Val |
| | | | | 215 | | | | 220 | | | | | | 225 |
| Gly | Asp | Ile | Leu | Asp | Leu | Pro | Asn | Leu | Arg | Glu | Val | Arg | Ala | Ala |
| | | | | 230 | | | | 235 | | | | | | 240 |
| Gly | Leu | Ser | Ser | Ala | Ala | Gly | Val | Ala | Ser | Ala | Glu | Gly | Met | Ala |
| | | | | 245 | | | | 250 | | | | | | 255 |
| Arg | Val | Tyr | Ala | Ala | Ala | Leu | Thr | Gly | Leu | Ala | Ala | Asn | Gly | Asp |
| | | | | 260 | | | | 265 | | | | | | 270 |
| Arg | Ala | Ala | Val | Ala | Pro | Leu | Leu | Ser | Glu | Glu | Thr | Ile | Gln | Thr |
| | | | | 275 | | | | 280 | | | | | | 285 |
| Val | Thr | Ala | Glu | Gln | Val | Phe | Gly | Ile | Asp | Arg | Val | Phe | Gly | Glu |
| | | | | 290 | | | | 295 | | | | | | 300 |
| Thr | Ser | Cys | Phe | Gly | Thr | Val | Phe | Met | Lys | Ser | His | Ala | Arg | Ser |
| | | | | 305 | | | | 310 | | | | | | 315 |
| Pro | Tyr | Gly | Ser | Tyr | Arg | Ala | Phe | Gly | His | Asp | Gly | Ala | Ser | Ala |
| | | | | 320 | | | | 325 | | | | | | 330 |
| Ser | Leu | Gly | Phe | Ala | Asp | Pro | Val | Tyr | Glu | Leu | Ala | Phe | Gly | Tyr |
| | | | | 335 | | | | 340 | | | | | | 345 |
| Val | Pro | Gln | Gln | Ala | Glu | Pro | Gly | Gly | Ala | Gly | Cys | Arg | Asn | Leu |
| | | | | 350 | | | | 355 | | | | | | 360 |
| Glu | Leu | Ser | Ala | Ala | Val | Arg | Lys | Ala | Val | Thr | Glu | Leu | Ala | Gln |
| | | | | 365 | | | | 370 | | | | | | 375 |

( 2 ) INFORMATION FOR SEQ ID NO:2:

( i ) SEQUENCE CHARACTERISTICS:
        ( A ) LENGTH: 2174 base pairs
        ( B ) TYPE: nucleic acid
        ( C ) STRANDEDNESS: double
        ( D ) TOPOLOGY: linear     ( i i ) MOLECULE TYPE: genomic DNA     ( v i ) ORIGINAL SOURCE:
        ( A ) ORGANISM: Arthrobacter globiformis
        ( B ) STRAIN: SC-6-98-28 (Ferm BP- 3618)

( i x ) FEATURE:
        ( A ) NAME/KEY: CDS
        ( B ) LOCATION: from 1 to 1125
        ( C ) IDENTIFICATION METHOD: E     ( x i ) SEQUENCE DESCRIPTION: SEQ ID NO:2:

```
GGTACCGCTA  CCTTTTCATG  CACCCCAGCG  GTGAGGACCT  GAAATTCCTG  TCACGCCTGG    60

TTTCCGAGGG  GAAACTGCAA  CCCGTGGTGG  ACAGCAGCTA  TCCGCTCGAA  AAGATCGGCG   120

ACGTTTCGCC  GCGCTGGAGC  AGGGACGCGC  CAAGGGCAAG  ATCGTGGTGA  CCATGGACAC   180

GCGCGGCAGT  TAGGCAGTTA  GGCTGTCCGG  GTGGATGCAC  AGACGATTGC  CCCTGGATTC   240

GAATCAGTCG  CCGAACTCTT  TGGCCGTTTC  CTGAGCGAAG  ACCGGAATA   TTCAGCCCAG   300

CTCGCGGCCT  ACCACCGCGG  AGTCAAGGTA  TTGGACATCA  GCGGTGGGCC  GCACCGCCGC   360

CCGGATTCCG  TGACCGGTGT  TTTCTCCTGC  TCCAAGGGAG  TATCCGGGCT  GGTCATCGCA   420
```

| | | | | | | |
|---|---|---|---|---|---|---|
|CTTTTGGTCC|AGGACGGCTT|CCTCGACCTC|GACGCCGAAG|TGGTCAAGTA|CTGGCCGGAA|480|
|TTCGGCGCCG|AAGGAAAGGC|CACGATTACC|GTGGCCCAGC|TGCTCTCCCA|CCAGGCCGGG|540|
|CTTCTGGGAG|TCGAAGGCGG|ACTCACCCTC|GCGGAATACA|ACAACTCCGA|ACTGGCCGCC|600|
|GCCAAGCTCG|CGCAGATGCG|GCCGCTGTGG|AAGCCCGGGA|CCGCCTTCGG|GTACCACGCC|660|
|CTGACCATCG|GCGTCTTCAT|GGAGGAGCTT|TGCCGCCGGA|TCACCGGGTC|CACGCTCCAG|720|
|GAAATCTACG|AACAGCGGAT|CCGCTCGGTC|ACGGGCGCCC|ACTTCTTCCT|GGGACTGCCT|780|
|GAGTCCGAGG|AACCCCGCTA|TGCCACCCTC|CGTTGGGCTG|CAGACCCCTC|CCAGCCGTGG|840|
|ATTGATCCCG|CCAGCCATTT|CGGCCTTTCC|GCAAACTCGG|CCGTGGGGA|CATCCTTGAC|900|
|CTGCCCAACC|TCCGCGAGGT|CCGCGCAGCC|GGCCTGAGTT|CAGCCGCCGG|AGTCGCCAGC|960|
|GCGGAAGGCA|TGCCCGCGT|CTACGCTGCG|GCACTCACCG|GACTTGCCGC|CAACGGCGAC|1020|
|CGAGCCGCCG|TCGCGCCCCT|CCTCAGCGAA|GAGACCATCC|AAACCGTCAC|GGCCGAGCAG|1080|
|GTCTTCGGCA|TCGACCGGGT|GTTCGGCGAG|ACGAGCTGCT|TTGGGACAGT|GTTCATGAAA|1140|
|TCGCATGCAC|GCTCGCCTTA|TGGCAGCTAC|CGGGCGTTCG|GGCACGACGG|CGCCAGCGCA|1200|
|TCTTTGGGGT|TCGCTGACCC|TGTGTATGAA|CTCGCCTTCG|GGTACGTGCC|GCAACAGGCC|1260|
|GAGCCGGGCG|GAGCGGGATG|CCGCAACCTT|GAGCTGAGCG|CCGCCGTGCG|GAAGGCAGTC|1320|
|ACCGAACTGG|CTCAGTAGGA|TGAAGCATGA|CCGAACCGAG|ATTCACCGTT|GAAACAGCCA|1380|
|TGGTCCTTGC|CGAAGTGGCG|CACAATCGCC|AGAAGGACAA|GCTGAAGCGG|CCGTACCGCG|1440|
|AGCACGTTCT|GGCGGTAGGG|GATGCGCTCG|CCGACTTCGA|CGACGACATC|CGGATCGCAG|1500|
|GTTACCTGCA|CGACATCGCC|AAGGACACGC|CGATTACCAA|GCAGGCGCTG|CTCGACATGG|1560|
|GTGTTTCCGA|GCGTGCCGTG|GGCATCATCG|AACGCGTGAC|GCGCCGATTC|CAGGATGATT|1620|
|CGGACAACGA|TGAAGCCGTC|GTTCTGCATA|TCGCACAGGA|CCATGACGCC|ACCCTGGTCA|1680|
|AGATCGCCTG|CAACGCCCAC|AACTCCGTGC|CGGAGCGCGT|GCGGGCGCTC|GCCGAAAAGT|1740|
|GGCCGGACAA|GGCACCCAGC|ACGCGCTACG|CAGACGCCCG|GGAAGTGCTC|TACAAGGCGG|1800|
|TGCCACGGGG|TGAAATCCAC|TTGGTCCTGC|AACGCATCAA|CCCTGATCTG|CTGTCCGAGA|1860|
|TGGACCGGCT|GGCGGACTAG|TAGTTCGACG|CGGCAGGTCT|CGCCTGTCTA|CGGTTTCGTC|1920|
|GGTTCGTCCT|GAATCGGGTT|GGCAGCGGCC|GCCGCCTCCC|GGGTAGCGGA|TGCGGTGACG|1980|
|TCCGCGAGAA|TCCGTTGGTG|GATCTGGGCG|GTGAGCTCGT|GAATCGCACG|CGTCAGGTCG|2040|
|GTGTTCTCCT|CGAGCAGATG|CTCCTGGGCG|TTGTAGTCAT|GGTCTGCCTT|CACCTGCTGG|2100|
|AAAGCCGCCT|GACGGTTCTG|TCCGATCATG|ACGAAGGTCG|AGAGGAAGAT|CGCTTCGAGC|2160|
|GAGACGATCA|AGGT| | | | |2174|

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: Other nucleic acid, synthetic DNA     ( x i ) SEQUENCE DESCRIPTION: SEQ ID NO:3:

GATCCTTTTT  TAATAAAATC                                         20

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single -continued   ( D ) TOPOLOGY: linear  ( i i ) MOLECULE TYPE: Other nucleic acid, synthetic DNA  ( x i ) SEQUENCE DESCRIPTION: SEQ ID NO:4:

TTTTACCTCC TGATTTTATT AAAAAAG                 27

( 2 ) INFORMATION FOR SEQ ID NO:5:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear  ( i i ) MOLECULE TYPE: Other nucleic acid, synthetic DNA  ( x i ) SEQUENCE DESCRIPTION: SEQ ID NO:5:

AGGAGGTAAA AAACGATGGA CGCACAGACC ATCGCACCGG GCTT      44

( 2 ) INFORMATION FOR SEQ ID NO:6:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear  ( i i ) MOLECULE TYPE: Other nucleic acid, synthetic DNA  ( x i ) SEQUENCE DESCRIPTION: SEQ ID NO:6:

CGAAGCCCGG TGCGATGGTC TGTGCGTCCA TCGTT            35

( 2 ) INFORMATION FOR SEQ ID NO:7:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear  ( i i ) MOLECULE TYPE: Other nucleic acid, synthetic DNA  ( x i ) SEQUENCE DESCRIPTION: SEQ ID NO:7:

TTTTTCCTCC TGATTTTATT AAAAAAG                 27

( 2 ) INFORMATION FOR SEQ ID NO:8:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear  ( i i ) MOLECULE TYPE: Other nucleic acid, synthetic DNA  ( x i ) SEQUENCE DESCRIPTION: SEQ ID NO:8:

AGGAGGAAAA AATCGATGGA CGCACAGACC ATCGCACCGG GCTT      44

( 2 ) INFORMATION FOR SEQ ID NO:9:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear  ( i i ) MOLECULE TYPE: Other nucleic acid, synthetic DNA  ( x i ) SEQUENCE DESCRIPTION: SEQ ID NO:9:

CGAAGCCCGG TGCGATGGTC TGTGCGTCCA TCGAT            35

(2) INFORMATION FOR SEQ ID NO:10:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: Other nucleic acid, synthetic DNA (xi) SEQUENCE DESCRIPTION: SEQ ID NO:10:

AGGAGGAAAA AATATGGACG CACAGACCAT CGCACCGGGC TT          42

(2) INFORMATION FOR SEQ ID NO:11:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ii) MOLECULE TYPE: Other nucleic acid, synthetic DNA (xi) SEQUENCE DESCRIPTION: SEQ ID NO:11:

CGAAGCCCGG TGCGATGGTC TGTGCGTCCA TAT          33